United States Patent [19]

McKee et al.

[11] Patent Number: 4,558,027
[45] Date of Patent: Dec. 10, 1985

[54] CATALYSTS FOR CARBON AND COAL GASIFICATION

[75] Inventors: Douglas W. McKee, Burnt Hills; Clifford L. Spiro, Scotia; Philip G. Kosky, Schenectady, all of N.Y.

[73] Assignee: The United States of America as represented by the United States Department of Energy, Washington, D.C.

[21] Appl. No.: 614,077

[22] Filed: May 25, 1984

[51] Int. Cl.[4] .......................... B01J 21/20; B01J 27/08; B01J 27/02; C01J 3/54

[52] U.S. Cl. .................................. 502/181; 48/197 R; 48/202; 502/174; 502/180; 502/218; 502/224

[58] Field of Search ............... 502/174, 180, 181, 184, 502/218, 224

[56] References Cited

U.S. PATENT DOCUMENTS

| | | | |
|---|---|---|---|
| 1,921,711 | 8/1933 | Wangemann | 48/206 |
| 2,672,410 | 3/1954 | Mattox | 48/206 |
| 3,252,773 | 5/1966 | Solomon et al. | 48/202 |
| 3,567,412 | 3/1971 | LeFrancois et al. | 502/218 |
| 3,689,240 | 9/1972 | Aldridge et al. | 502/174 |
| 4,069,304 | 1/1978 | Starkovich et al. | 48/206 |
| 4,094,650 | 6/1978 | Koh et al. | 48/202 |
| 4,318,712 | 3/1982 | Lang et al. | 48/202 |
| 4,336,034 | 6/1982 | Lang et al. | 48/206 |

OTHER PUBLICATIONS

*Chemical Engineering* 3/22/82—pp. 64-66, "Methane from Coal Aided by Use of Pottasium Catalyst", by L. J. Kaplan.

*Carbon*—1975—vol. 13—pp. 381-390—"The Catalytic Behavior of Alkali Metal Carbonates and Oxides in Graphite Oxidation Reactions", by D. W. McKee and D. Chartterji.

*Primary Examiner*—P. E. Konopka
*Attorney, Agent, or Firm*—Earl L. Larcher; Stephen D. Hamel; Judson R. Hightower

[57] ABSTRACT

Catalyst for the production of methane from carbon and/or coal by means of catalytic gasification. The catalyst compostion containing at least two alkali metal salts. A particulate carbonaceous substrate or carrier is used.

5 Claims, 10 Drawing Figures

CATALYSTS FOR CARBON AND COAL GASIFICATION

BACKGROUND OF THE INVENTION

1. Field of the Invention and Contract Statement

The invention relates to improved catalysts for carbon and coal gasification and improved processes for catalytic, coal gasification. The United States Government has rights in this invention pursuant to Contract No. DE-AC21-80MC14591 between the U.S. Department of Energy and General Electric Co.

2. Discussion of Background and Prior Art

Coal has been converted to methane using the thermal-gasification scheme wherein coal was reacted with steam at a high temperature (925° C.) to produce synthesis gas ($CO+H_2$), which then underwent additional reactions at a lower temperature (425° C.), producing $CH_4$ and $CO_2$. The reactions include a "water gas shift" (required because the proportions of CO and $H_2$ produced in the gasification were different from what was needed in the next step), and a methanation. This method resulted in significant inefficiencies because the temperature of the second stage was lower than that of the first; therefore, the heat liberated by the methanation could not be used to provide the high-temperature heat required for the gasification.

Alkali-metal salts of weak acids (e.g., $K_2CO_3$ and $Na_2CO_3$) have been used to catalyze the steam gasification of coal. Increasing the amount of $K_2CO_3$ on charcoal increased the quantity of synthesis gas produced when the mixture was reacted with steam at a constant temperature. Commercially acceptable gasification rates can be obtained at a lower temperature (700° C.) with a $K_2CO_3$ catalyst (with concentrations of 10 to 20 percent by weight) than without a catalyst (925° C.).

*Chemical Engineering,* "Methane From Coal Aided By Use Of Potassium Catalyst", Mar. 22, 1982, pp. 64 to 66, teaches that potassium catalyst on char (coal that has been partially depleted of carbon and hydrogen) catalyzed the methanation reaction at 700° C., the temperature at which the catalyzed gasification takes place. If the catalysis could be carried out at 400° C., there would be negligible $H_2$ and CO at equilibrium, and no recycle would be necessary. In addition to yielding the required product, $CH_4$, it was not necessary to supply reaction heat to the gasifier (except for enough heat to raise the temperature of the recycle gases before they enter the gasifier). However, the selectivity of the overall reaction could not be achieved by chemistry alone at this temperature; recycle and separation steps were required. The $H_2$ and CO were separated and recycled to the gasifier so that there were no net formation of endothermic products. In one longterm run, the gasifier was operated at 500 p.s.i.g. and 690° C., with the following results; steam conversion was 35 percent, carbon conversion ran 85 to 90 percent and the average methane content of the product gas reached 20 to 25 percent.

U.S. Pat. No. 3,567,412 teaches a method for improving the gasification and combustion rates of carbonaceous materials in a reaction zone containing a melt, which is an alkali metal carbonate. At least a critical minimum concentration of 0.4 weight percent of sodium sulfate is maintained in the reaction melt. Also, the viscosity of the melt is maintained between about 10 and about 150 centipoises.

U.S. Pat. No. 1,921,711 discloses a process for producing water-gas. Carbonaceous fuel is heated on a bath of molten sodium chloride to the temperature of bath. Steam is introduced into the heated fuel, whereby water-gas is produced.

U.S. Pat. No. 3,252,773 discloses a process for the production of hydrogen-containing gas from a solid carbonaceous material and steam. Alkali metal carbonate is charged to a reaction zone. The alkali metal carbonate is maintained in molten form in the reaction zone as the reaction medium. The alkali metal carbonate constitutes at least 75 weight percent of the reaction medium. The reaction medium is maintained at a temperature between 800° and 1800° F. A solid carbonaceous material and steam are introduced into molten reaction medium in which the solid carbonaceous material and steam react to produce a gaseous product containing hydrogen and an oxide of carbon. Gaseous effluent containing the hydrogen and an oxide of carbon is withdrawn from the reaction zone.

U.S. Pat. No. 2,672,410 teaches a process for the production of gas mixtures containing $H_2$ and CO by reacting solid carbonaceous materials simultaneously with steam and oxygen in a gasification zone. An extraneous metal halide (yielding a reaction product which is elemental halogen and volatile halogen compounds) is added at the reaction conditions. The halide is present in an amount providing a halogen equivalent corresponding to that of about 0.01 to 1 percent by weight of alkali metal halide based on the carbon present. Such amount is adequate to inhibit the formation of $CO_2$ in favor of CO formation.

U.S. Pat. No. 4,336,034 discloses contacting carbonaceous solids in the presence of water with potassium sulfate and a calcium compound which is calcium oxide, calcium hydroxide, and calcium carbonate. The treated carbonaceous solids are then gasified. The calcium compound apparently activates the relatively noncatalytic potassium sulfate, thereby producing a substantial catalytic effect on the gasification reactions.

U.S. Pat. No. 4,069,304 discloses catalytically reacting coal steam to produce hydrogen. Various Group I metal salts, such as $K_2CO_3$, $Na_2CO_3$ and borax, are used as catalysts. The catalysts are stabilized with fluoride-containing salts such as $CaF_2$ to thereby extend their life. Also, NaF by itself is a thermally stable catalyst for the reaction.

McKee, D. W., and D. Chatterji, *Carbon,* 13(5), 381 (1975), teaches that, in alkali-catalyzed oxidation reactions of graphite, the oxidation rates increased rapidly in the vicinity of the melting point of the active catalyst phase.

SUMMARY OF THE INVENTION

An object of the invention is to provide an improved process for the catalytic gasification of coal and other carbonaceous material to methane. Another object of the invention is to provide an improved catalyst for such process. Other objects and advantages of the invention are set out herein or are obvious herefrom to one ordinarily skilled in the art.

The objects and advantages of this invention are achieved by the improved eutectic system of the invention.

To achieve the foregoing and other objects in accordance with the purpose of the invention, as embodied and broadly described herein, the invention involves an improved process for the production of methane from coal or carbon by means of catalytic gasification of the coal or carbon. The area of the invention is termed catalytic coal char gasification.

Preferably the catalyst composition contains an alkali metal carbonate or an alkali metal sulfate and at least one further alkali metal salt.

Preferably the alkali metal carbonate is sodium carbonate or potassium carbonate. Also, preferably the further alkali metal salt is an alkali metal carbonate other than the required alkali metal carbonate. Preferably the further alkali metal salt is an alkali metal halide.

The catalyst composition is used preferably in an amount of about 1 to about 20 weight percent, based on the total weight of the catalyst composition of the coal and/or carbon. Preferably the catalytic gasification is conducted at a temperature of about 575° to about 725° C. and at a pressure of about 350 to about 700 p.s.i.g., and utilizes as hydrogen, carbon monoxide and steam in the feed and/or recycle.

Preferably particulate, the carbonaceous carrier is particulate coal or particulate coal char. Preferably the eutectic catalyst composition is located on and/or in the particulate, carbonaceous carrier.

The invention also involves an improved catalyst for use in the process of producing methane from carbon and/or coal. The catalyst has a eutectic catalyst composition containing at least two alkali metal salts, and a particulate carbonaceous substrate or carrier.

Preferably the catalyst includes a eutectic catalyst composition containing an alkali metal carbonate or an alkali metal sulfate and at least one further alkali metal salt, and a particulate carbonaceous substrate or carrier.

Preferably the alkali metal carbonate is sodium carbonate or potassium carbonate. Also, preferably, the further alkali metal salt is an alkali metal carbonate other than the required alkali metal carbonate. The further alkali metal salt is preferably an alkali metal carbonate other than sodium carbonate or potassium carbonate.

Preferably the further alkali metal salt is an alkali metal halide, which preferably is an alkali metal chloride or alkali metal fluoride. Preferably the alkali metal sulfate is sodium sulfate. Advantageously the eutectic catalyst composition is a binary eutectic salt composition or is a tertiary eutectic salt composition.

The eutectic composition most preferably is:
(a) a NaCl—$Na_2CO_3$ eutectic composition,
(b) A NaCl—$Na_2SO_4$ eutectic composition,
(c) A KF—$K_2CO_3$ eutectic composition,
(d) a KCl—$K_2CO_3$ eutectic
(e) a $LiCO_3$—$Na_2CO_3$—$K_2CO_3$ eutectic composition,
(f) a $Na_2SO_4$—NaCl—$Na_2CO_3$ eutectic composition, or
(g) a LiF—$Li_2CO_3$ eutectic composition.

The particulate, carbonaceous carrier preferably is particulate coal or particulate coal char. Preferably the eutectic catalyst composition is located on and/or in the particulate, carbonaceous carrier. Advantageously, the eutectic catalyst composition is present in an amount of about 1 to about 20 weight percent, based on the total weight of the eutectic catalyst composition and the particulate carbonaceous carrier.

In order for a catalyst to function satisfactorily in carbon/char gasification scheme a three-phase interface must be maintained between the carbonaceous substrate, the catalyst phase and the gaseous oxidant. Whatever the detailed mechanism of the catalytic process, overall rates of gasification are enhanced by increasing the catalyst-carbon interfacial area, as long as the gaseous oxidant still has ready access to this interface. For this reason, the melting of the eutectic salt catalyst phase promotes catalyst reactivity by spreading of the molten droplets over the substrate and promotes better contact between catalyst and carbon. However, if the carbonaceous surface is smothered by a film of molten catalyst, the kinetics will be limited by diffusion of the gaseous reactant through the film of salt and the overall rates and apparent activation energies of the gasification process will be reduced.

The binary and ternary eutectics, which melt at significantly lower temperatures than the pure salt constituents, show enhanced catalytic activity for the carbon-steam and carbon-$CO_2$ reactions in the coal gasification scheme.

Reference will now be made in detail to the present preferred embodiments of the invention, examples of which are illustrated in the accompanying drawings.

A BRIEF DESCRIPTION OF THE INVENTION

The accompanying drawings, which are incorporated in and from a part of the specification, illustrate the invention, and together with the description, serve to explain the principles of the invention. In the drawings.

DETAILED DESCRIPTION OF THE INVENTION

All parts, percentages ratios and proportions are on a weight basis unless otherwise stated herein or obvious herefrom to one ordinarily skilled in the art.

Figure 1:
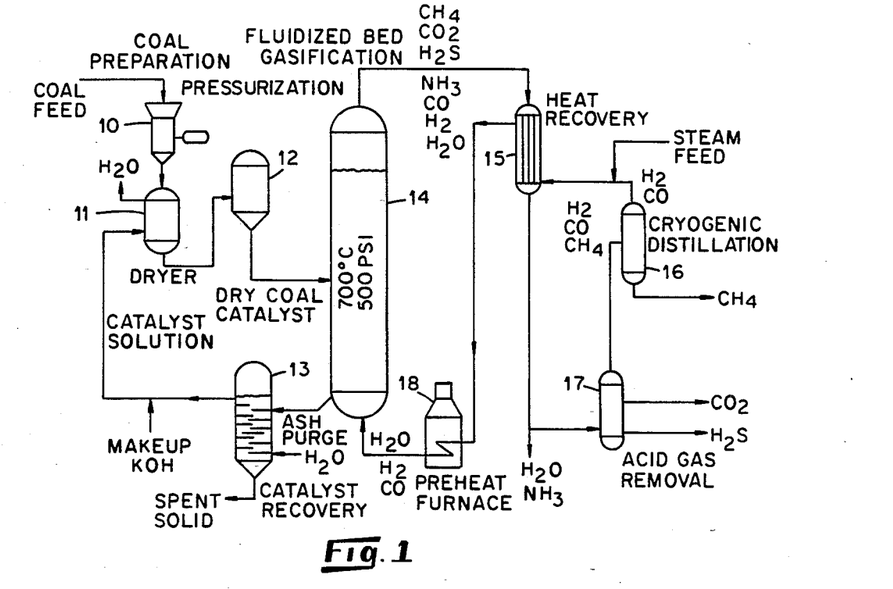
FIG. 1 is a schematic diagram of the process of catalytic, gasification production of methane from coal.
Figure 2:
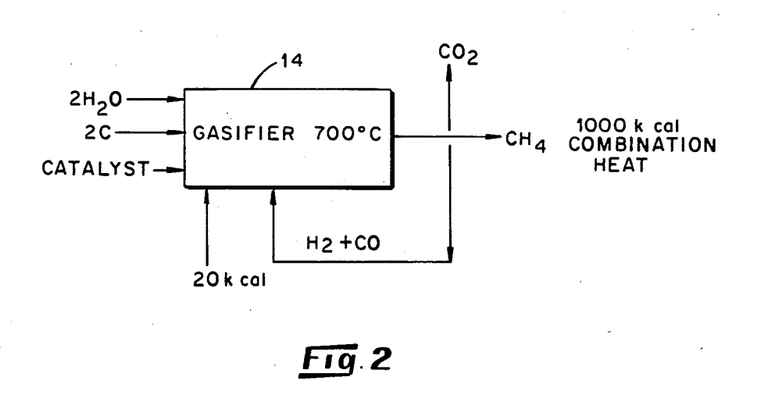
FIG. 2 is a schematic diagram fluidized-bed gasifier used in the process shown in FIG. 1.

Referring to FIG. 1, a schematic diagram of the catalytic, gasification production of methane from coal is shown. The process combines two reaction steps, namely, gasification and methanation, in one fluidized-bed reactor to produce methane (that is, synthetic natural gas). The invention process uses the invention catalyst to selectively produce methane by reacting coal and steam at one temperature and in a fluidized-bed reaction vessel. The overall simplified reaction using carbon follows:

$$2C + 2H_2O = CH_4 + CO_2$$

When the equation is written for coal, which contains hydrogen, the equation becomes:

$$1.2H_2O + 1.7CH_{0.9}O_{0.1} = CH_4 + 0.7CO_2$$

The process consists of four main operations; coal preparation, fluidized-bed gasification, catalyst makeup and recovery, and product separation and recovery. The process allows the reactions to take place in a single reactor.

The coal, crushed to a size suitable for fluidization (approximately 1 to 2 mm) is mixed with an aqueous solution of the eutectic composition of the invention to yield approximately 8 percent (by weight) of catalyst of the coal. Dried and pressurized, the coal is fed through a series of lock hoppers to the gasifier, which usually operates at 600° C. and 500 p.s.i.g. (35 atm).

Coal is a complex and variable metamorphosed rock which is composed basically of two types of materials, that is, the macerals or carbonaceous remains of plants constitute the organic fraction of coal, with the remainder comprised of minerals or inorganic impurities present in the parent vegetation or deposited subsequently. The reactivity and properties of coal can be profoundly influenced by these inorganic impurities. Coal is quite heterogeneous.

If coal char is used, the catalyst can be placed on the coal before pyrolysis or on the coal char after pyrolysis of the coal.

The catalyst composition is used in an amount which is effective to achieve the reactions of the invention process. Preferably about 2 to about 12 weight percent, based on the total weight of the catalyst composition and the coal and/or carbon, of the catalyst composition can be used. The coal serves as a carrier or substrate for the catalyst. If desired catalyst-carrying coal particles or coal char particles can be mixed with the main coal or coal char charge for the gasifier.

The carbonaceous material is introduced into the gasification zone at a rate within the range from about 0.001 to about 5 pounds of carbonaceous material per hour per pound eutectic catalyst composition. In any particular instance, the amount of carbonaceous material introduced will depend upon the percentage of carbon contained therein. In the gasifier, the primary reactions are steam, hydrogen and CO$_2$ gasification (the last is also known as the Boudouard reaction), respectively:

$$C + H_2O = CO + H_2$$

$$C + 2H_2 = CH_4$$

$$C + CO_2 = 2CO$$

Usually, the gasifier melting zone is pre-heated at a temperature of about 500° to about 800° C., preferably between about 575° and about 625° C. The reactions can be carried out in the gasifier under a pressure between about 15 and about 2000 p.s.i.a. although pressures between about 200 and about 600 p.s.i.a. are more desirable. The proportion of steam reactant introduced into the gasifier is maintained between about 1 and about 10 moles of steam per mole of carbon with the preferred steam to carbon ratio being between about 1.1 and about 2.0 moles of steam per mole of carbon.

It is in the gasifier that the coal fluidized by gases at a velocity of, say, about 30 cm/s reacts with steam to produce CH$_4$ and CO$_2$ as net products. The raw-gas product also contains unreacted H$_2$ and CO plus steam as major constituents. Sulfur and nitrogen in the coal appear as minor quantities of H$_2$S and NH$_3$. In addition, the exiting gas contains fines of unreacted coal and ash that are separated by a cyclone and returned to the bed.

The operation of a catalyzed coal gasification plant at a temperature of 600° C., rather than 700° C., results in substantial cost savings and increased yields of methane as the methanation reaction becomes more favorable at lower temperatures.

A combination of heat recovery (the 1,300° F. gases are cooled to about 500° F.) and wet scrubbing removes the H$_2$O, NH$_3$ and entrained particulates. A conventional solvent process for acid scrubbing removes the H$_2$S and CO$_2$. Separation of the methane from the unreacted H$_2$ and CO takes place in a cryogenic distillation unit, with the CO and H$_2$ being recycled back to the gasifier after being mixed with steam and preheated to the reaction temperature of a gas-fired furnace.

Any form or version of catalytic gasification processes for the production of methane can be used in conjunction with the invention eutectic catalysts.

The invention eutectic catalysts melt and both pit and channel on graphite under gasification conditions. The graphite surface is somewhat poorly wetted by the molten catalyst. The invention eutectic catalyst melt and both pit and channel on coal char (anthracite) under gasification conditions. The char surface is better wetted than graphite by the molten catalyst. Dry catalysts in the form of micronized powder (consisting of aggregates of about 10 microns with about 1 micron particles detectable) can be added to the coal char particles. (The invention eutectic catalysts are solid at room temperature). Preferably the invention catalyst is added to the coal char particles in the form of a saturated aqueous solution of the invention eutectic catalyst composition and then the water driven off by drying. (The admixture of saturated solution and char particles can be subjected to pressure for a period of time to help drive the solution into the char particles). This scheme disperses the catalyst on and in the coal char particles.

Residual solids (ash and unreacted coal) can be continuously removed from the gasifier and the catalyst recovered. This is accomplished by means of a staged, countercurrent water-wash process. Because some of the catalyst reacts with clay minerals in the coal ash to form insoluble catalytically-inactive alkali aluminosilicates, makeup catalyst is added to the recovery solution.

The process shown in FIG. 1 involves coal preparation where coal is fed into feeder 10 and then dried in drier 11. Catalysts solution from catalysts recovery unit 13 is admixed with the coal in drier 11. The dried catalysts were fed into pressurizer 12 and then into fluidized bed gasifier 14. The gasifier 14 is operated at a temperature of 700° C. and 500 p.s.i. Water, hydrogen, and carbon monixide coming from heat recovery unit 15 are preheated in preheating furnace 18 and fed into gasifier 14. The material from the bottom of gasifier 14 is purged into the catalysts recovery unit 13. The catalysts resultant from gasification reaction in gasifier 14 are fed into heat recovery unit 15 as previously stated. Water, hydrogen and carbon monoxide are removed and recycled to gasifier 14. The materials removed from the bottom of heat recovery unit 15 are fed to acid gas removal 17 and cryogenic distillation 16 to remove water, ammonia, hydrogen sulfate and carbon dioxide, in order to recover the desired product, methane.

The reactivity of carbon towards dioxide and steam is known to be enhanced by the presence of alkali metal salts. In processes for the catalyzed gasification of coal, by the use of suitable catalysts, the gasification rate of coal char at a given temperature can be significantly increased; or alternatively, the processes can be operated at substantially lower temperatures than in the absence of a catalyst. Potassium carbonate appears to be the best prior art catalyst for this application. For a catalyst to function satisfactorily in carbon/char gasification, three component contacts must be maintained among the carbonaceous substrate, the catalyst phase and the gaseous reagent. Whatever the detailed mechanism of the catalytic process, overall rates of gasification would be expected to be enhanced by increasing the catalyst-carbon interfacial contact, as long as the gaseous oxidant still has ready access to this interface.

The invention is based, in part, on the discovery low melting point binary and ternary eutectic salt compositions having significantly greater catalytic activity in carbon/char gasification than potassium carbonate alone. Melting of the catalyst phase at reduced temperatures promotes catalyst reactivity by spreading of the molten droplets over the substrate and by promoting better contact between catalyst and carbon.

As used herein, the term alkali metals (i.e., Group IA metals) includes Na, K, Cs and Li. Examples of alkali metal carbonates which can be used in the invention catalytic eutectic compositions are $Cs_2CO_3$, $K_2CO_3$, $Na_2CO_3$, $Li_2CO_3$ and $Rb_2CO_3$. Examples of alkali metal sulfates which can be used in the invention $Na_2SO_4$, $K_2SO_4$, $Cs_2SO_4$ and $Li_2SO_4$. Examples of alkali metal halides, which can be used in this invention, are KCl, NaCl, KF, LiCl and NaF. (Salts of Li and Cs tend to be readily hydrolyzed to the hydroxides in the presence of water vapor at elevated temperatures).

Some of the preferred catalyst compositions of eutectic salts, the expected melting point of the salt phase of such preferred catalyst compositions, and the preferred initial composition of the catalyst/carbon materials are as follows in Table I:

TABLE I

| Eutectic Catalyst Compositions | | |
|---|---|---|
| Eutectic Salt Composition (mole %) | m.p., °C. | Eutectic Salt Composition/Carbon (Wt. %) |
| NaCl-60 m. % $Na_2CO_3$ | 640 | 4.2% NaCl; 5.8% $Na_2CO_3$ |
| NaCl-65 m. % $Na_2SO_4$ | 610 | 3.1% NaCl; 6.9% $Na_2SO_4$ |
| KF-40 m. % $K_2CO_3$ | 690 | 3.9% KF; 6.1% $K_2CO_3$ |
| KCl-35 m. % $K_2CO_3$ | 640 | 5.0% KCl; 5.0% $K_2CO_3$ |
| $Li_2CO_3$-31.5 m. % $Na_2CO_3$-25% $K_2CO_3$ | 397 | 3.2% $Li_2CO_3$; 3.3% $Na_2CO_3$; 3.5% $K_2CO_3$ |

All of the preferred binary eutectic catalysts exhibited activities are at least 3 to 5 times greater than that of the most active constituent of the mixture. Other preferred catalyst compositions of eutectic salts are $LiF/Li_2CO_3$ and $Na_2SO_4/NaCl/Na_2CO_3$. A preferred ternary eutectic, alkali carbonate catalyst is composed 43.5 m/o $Li_2CO_3$, 31.5 m/o $Na_2CO_3$ and 25.0 m/o $K_2CO_3$, 400° C.

Alkaline earth salts, such as, those of Ba, Ca and Sr, are less effective and much slower catalysts than alkali metal salts (of a given anion).

Successful experiments have been run using both graphite and chars prepared from Illinois No. 6 and Pittsburgh seam coals. Examples of other suitable coals are Reading anthracite, San Juan subbituminous. North Dakota lignite A—even graphite can be used. The coals and carbon are best used in char form.

Broadly, the solid carbonaceous feed material of the invention includes any of the various grades of coal such as anthracite, subbituminous, bituminous, brown coal, cannel coal, lignite, lignitic coal, coke from coal, coke from petroleum, peat, graphite, charcoal, wood and non-woody materials. Such materials may be used in lump, granular, finely divided or pulverized form.

Figure 3:
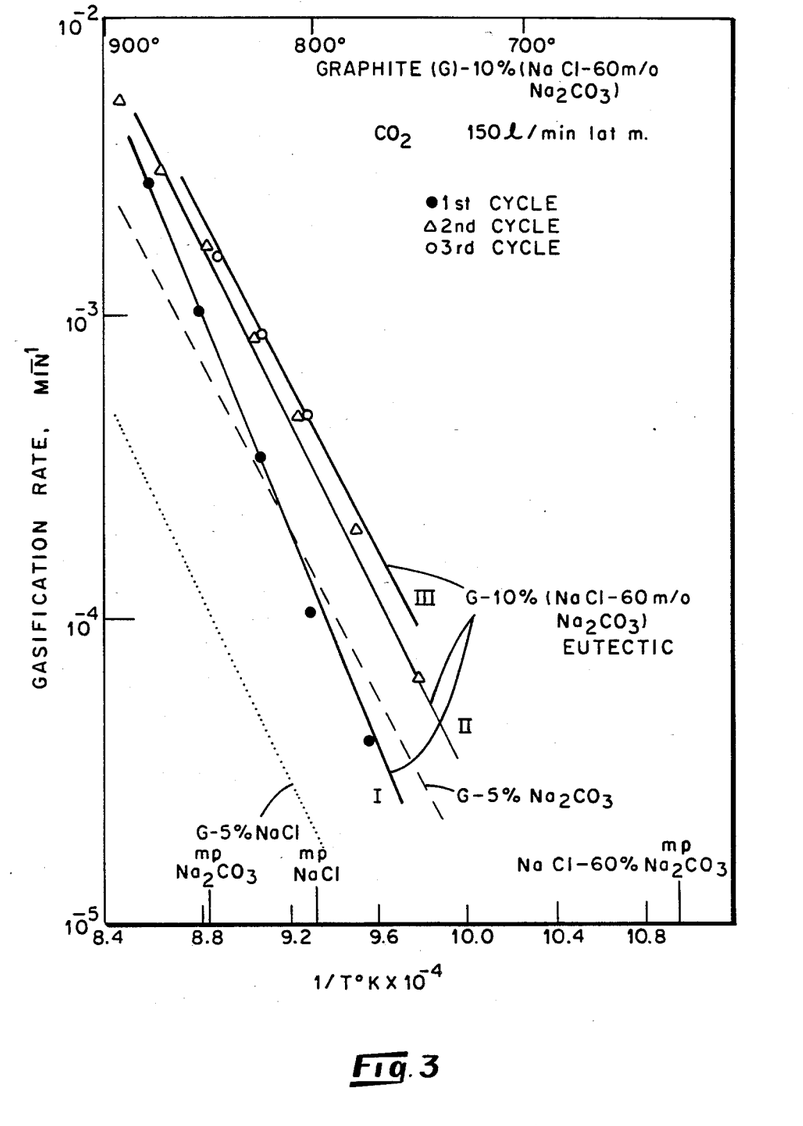
FIG. 3 is a plot of the catalytic activity of the NaCl—$Na_2CO_3$ eutectic for gasification of graphite in $CO_2$, i.e., gasification rate vs. 1/temperature, for successive thermal cycles.

FIG. 3 shows Arrhenius plots (log rate vs. 1/T for the gasification of graphite doped with 10 wt. percent of the NaCl—$Na_2CO_3$ eutectic. Data for graphite-5 percent NaCl and graphite-5 percent $Na_2CO_3$ are also shown for comparison purposes. During the first gasification trial, referred to as a thermal cycle, the binary catalyst showed activity roughly similar to that expected for a physical mixture of the two salt constituents at the same concentration. On subsequent cycles, i.e., repeat trials with the same sample, the catalytic activity of the binary salt increased as the eutectic phase melted and became more highly dispersed on the graphite surface. During the third thermal cycle, catalyzed gasification rates were more than three times greater than those of $Na_2CO_3$ alone at temperatures below 800° C.

Figure 4:
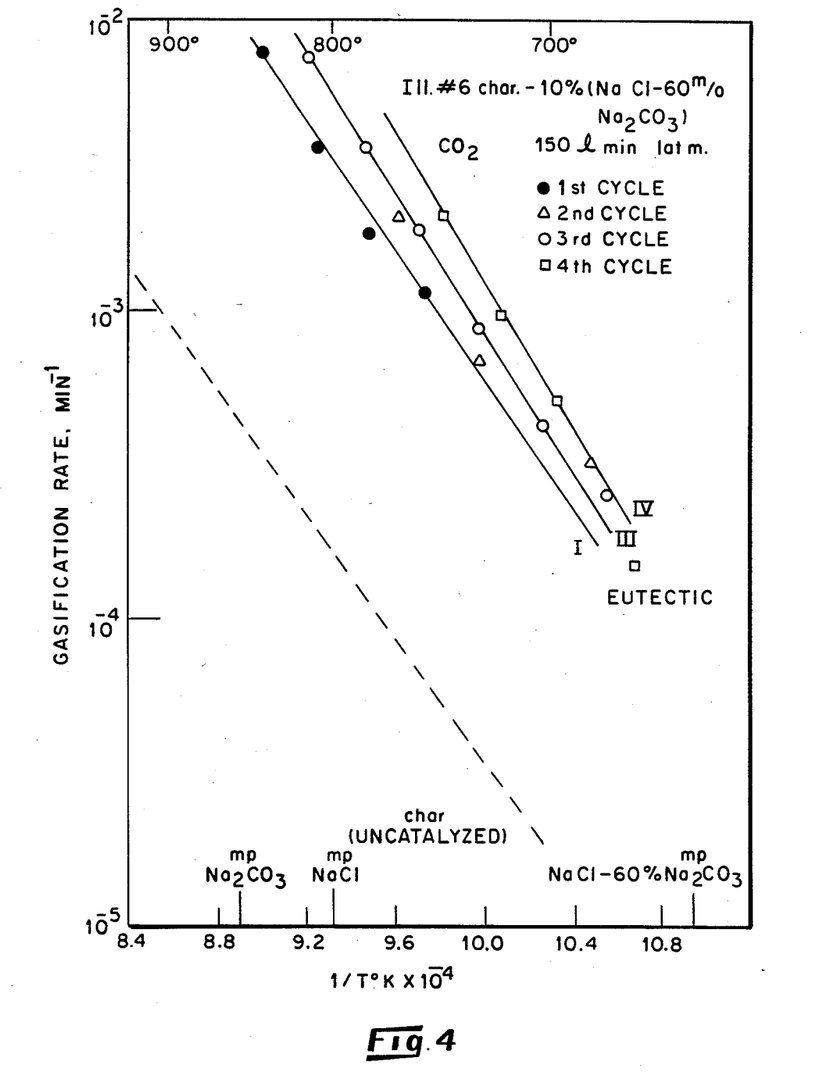
FIG. 4 is a plot of the catalytic activity of the NaCl—$Na_2CO_3$ eutectic for gasification of Illinois No. 6 char in $CO_2$, i.e., gasification rate vs. 1/temperature, for successive thermal cycles.

FIG. 4 shows a progressive increase in the catalytic activity of the binary NaCl—$Na_2CO_3$ catalyst with Illinois No. 6 char, the activity of the binary eutectic being about four times that of $Na_2CO_3$ alone below 800° C. At these temperatures the eutectic phase is in the molten state, whereas pure $Na_2CO_3$ is below its melting point.

Figure 5:
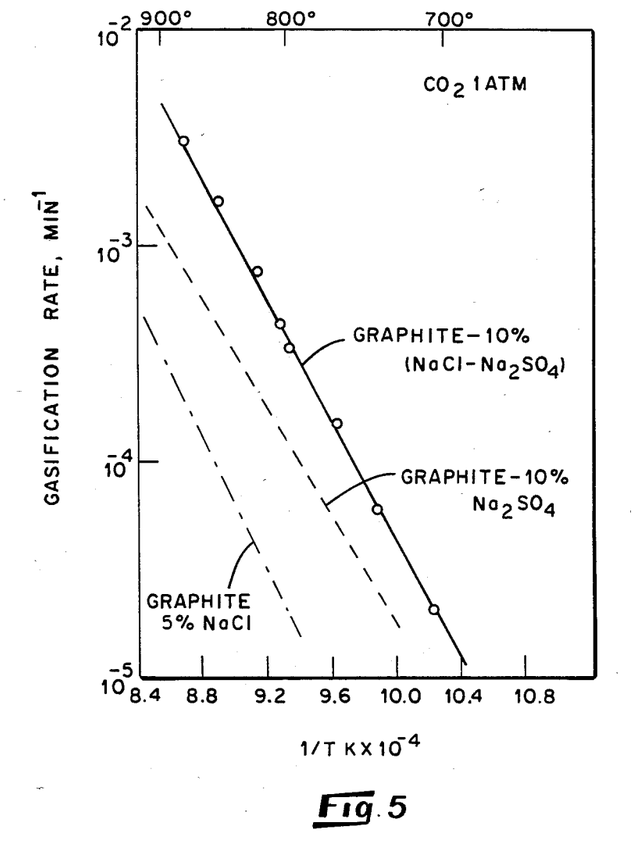
FIG. 5 is a plot concerning the $CO_2$ gasification of NaCl—$Na_2SO_4$ eutectic—catalyzed graphite and comparison to pure components.
Figure 6:
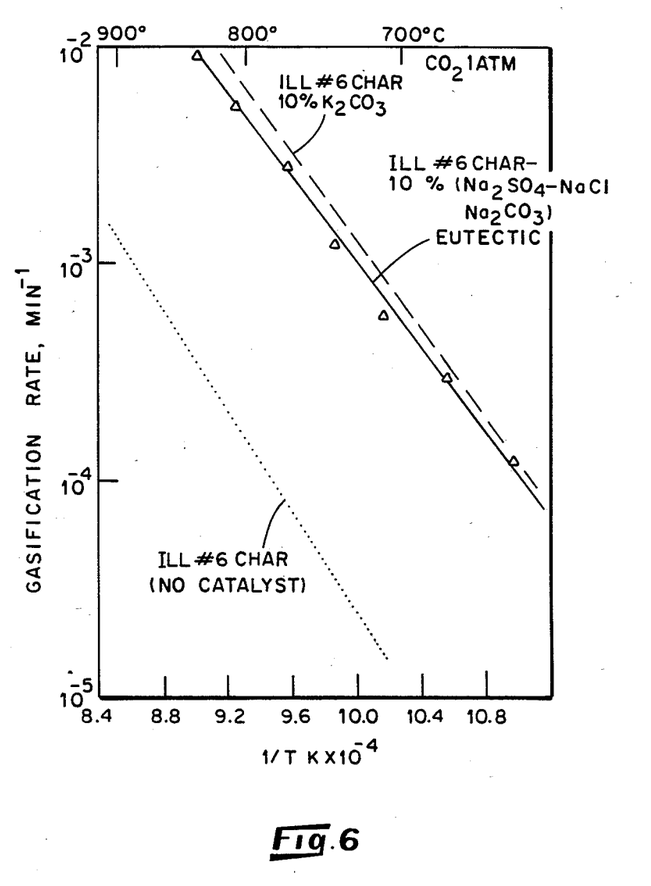
FIG. 6 is a plot concerning the $CO_2$ gasification of $Na_2SO_4$—NaCl—$Na_2CO_3$ eutectic—catalyzed Illinois No. 6—derived char.
Figure 7:
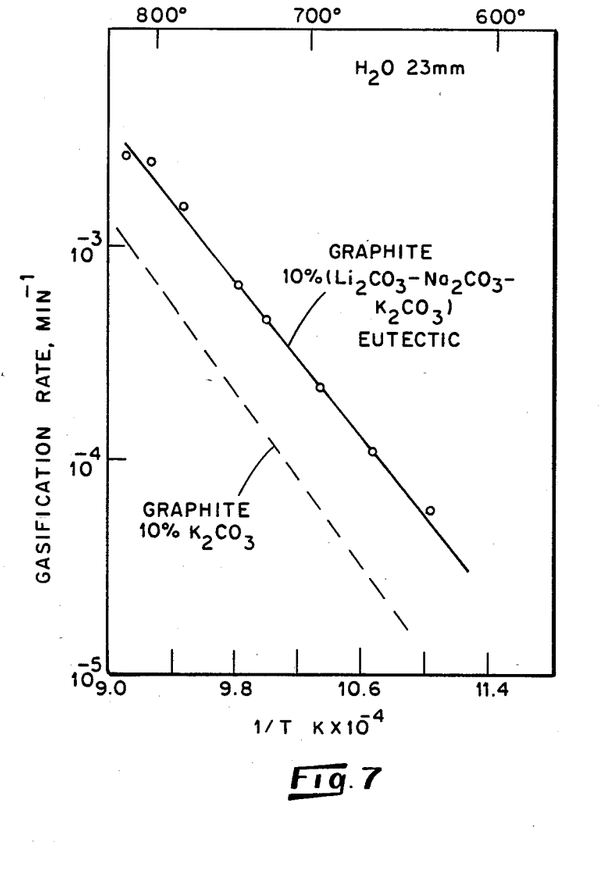
FIG. 7 is a plot concerning the $H_2O(g)$ gasification of $Li_2CO_3$—$Na_2CO_3$—$K_2CO_3$ eutectic—catalyzed graphite.
Figure 8:
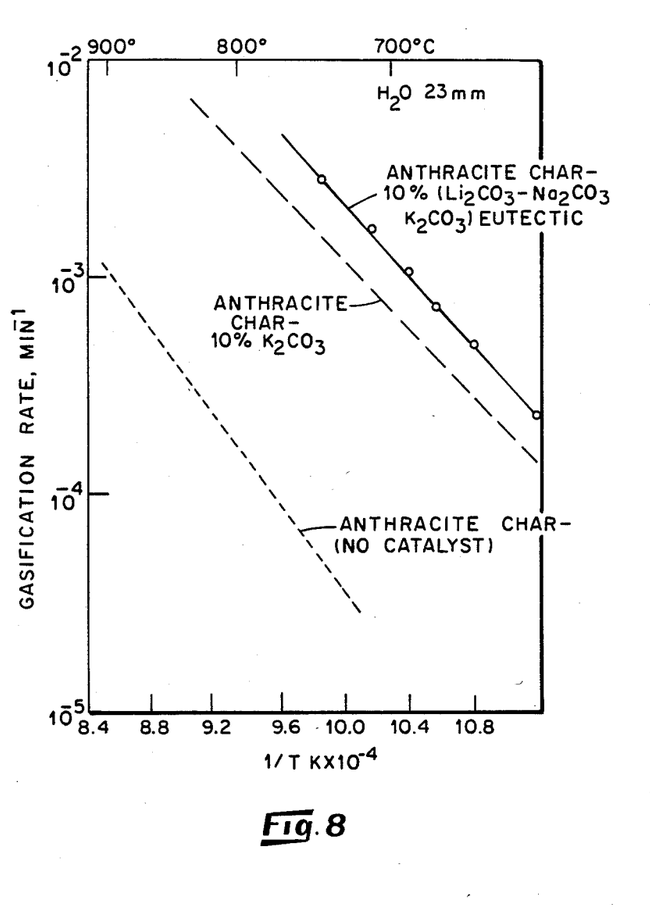
FIG. 8 is a plot concerning the $H_2O(g)$ gasification of $Li_2CO_3$—$Na_2CO_3$—$K_2CO_3$ eutectic—catalyzed anthracite char.
Figure 9:
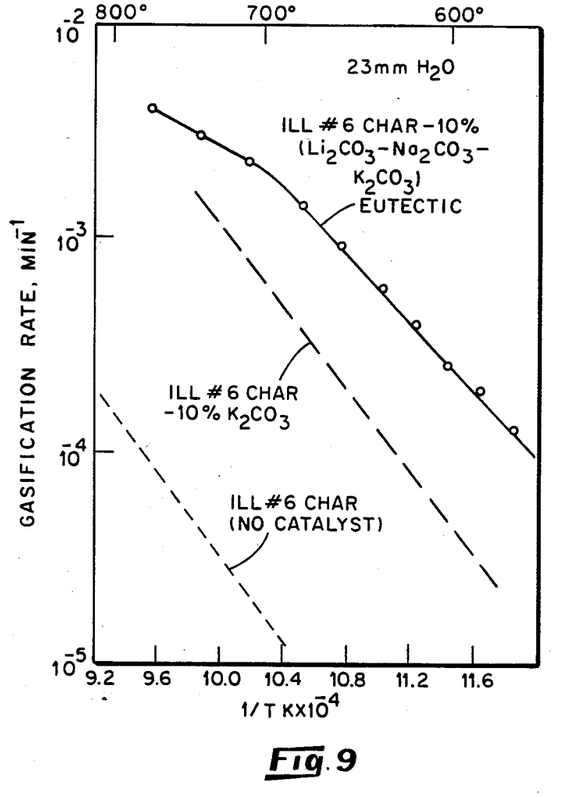
FIG. 9 is a plot concerning the $H_2O(g)$ gasification of $Li_2CO_3$—$Na_2CO_3$—$K_2CO_3$ eutectic—catalyzed Illinois No. 6 char.
Figure 10:
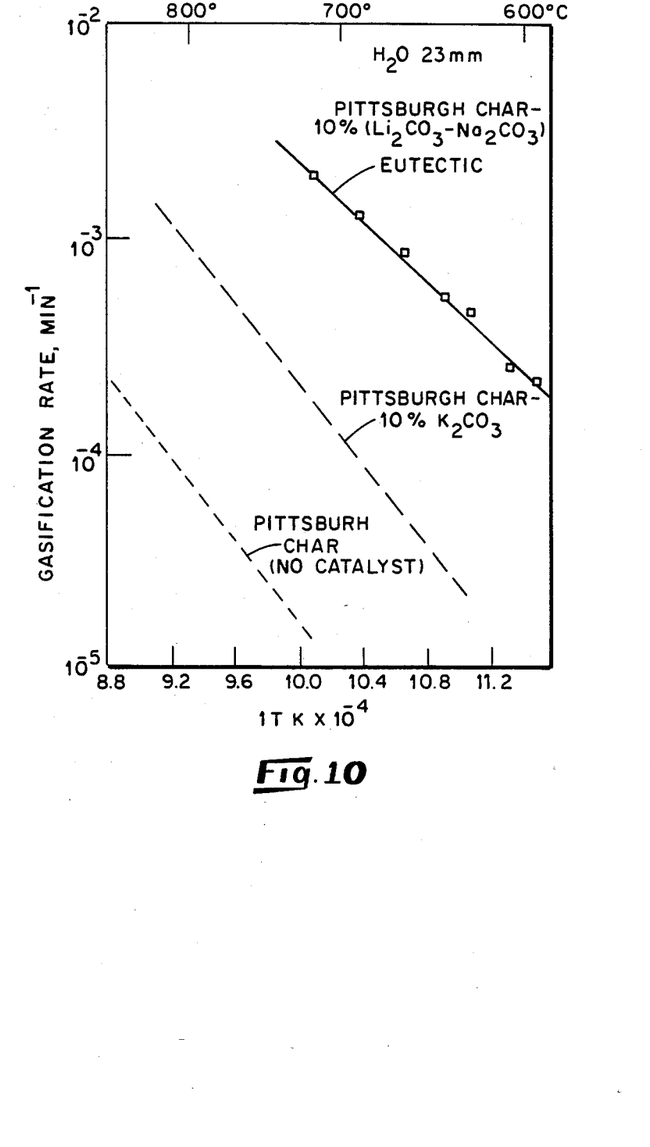
FIG. 10 is a plot concerning the $H_2O(g)$ gasification of $Li_2Co_3$—$Na_2CO_3$—$K_2CO_3$ eutectic—catalyzed Pittsburgh char.

FIG. 5 shows an Arrhenius plot for $CO_2$ gasification of graphite doped with 10 wt. percent of the NaCl—$Na_2SO_4$ binary eutectic (m.p. 610° C.). The observed rates were greater than for graphite-10 percent $Na_2SO_4$ by a factor of more than two, and more than an order of magnitude greater than graphite—5 percent NaCl. FIG. 6 shows $CO_2$ kinetic data for an Illinois char doped with 10 wt. percent of the $Na_2SO_4$—NaCl—$Na_2CO_3$ ternary eutectic (m.p. 612° C.). In this case, the catalytic activity was very similar to that exhibited by 10 wt. percent of $K_2CO_3$ under the same conditions. Data for the steam gasification reaction, catalyzed by the $Li_2CO_3$—$Na_2CO_3$—$K_2CO_3$ ternary eutectic (m.p. 400° C.) are shown in FIGS. 7 to 10 for a suite of coal chars of differing rank and for graphite. Because of the progressive decrease in reactivity observed during the first two thermal cycles, as a result of reaction of the alkali salts with coal minerals, data are compared for the third thermal cycles in each case. This ternary catalyst showed consistently higher activity than pure $K_2CO_3$ (at the 10 wt. percent level) with the greatest improvement exhibited by the Pittsburgh char and the least for the char derived from anthracite.

These results demonstrate that the melting point of the salt is an important variable in achieving efficient dispersion of the catalyst phase throughout the char substrate.

The invention eutectic catalysts also show enhanced activity for the char-steam reaction at low temperatures. In particular, the ternary $Li_2CO_3$—$Na_2CO_3$—$K_2CO_3$ eutectic, which melts at the very low temperature of 397° C., proved to be about ten times more active for the gasification of Pittsburgh char in steam than pure $K_2CO_3$ under the same conditions.

The coal can first be placed in the form of a char before it is used, but it should be noted that the pore structure of chars is a strong function of the molecular composition of the parent coal. Coals can be prepared for charring for example, in physical states of aggregation such as a micronized product and as grit-sized particles. The former is prepared in a fluid energy mill driven by $N_2$ gas to prevent aerobic attack on the fine coal particles. The grit coal has the typical size distribution:

| Particle Size in Microns | Wt. % of Total Distribution |
| --- | --- |
| 1000+ | 17.86 |
| 210–1000 | 62.74 |
| 75–210 | 14.22 |
| −75 | 5.18 |

Pore structure is a strong determinant of char reactivity; and the precise pore structure is a function of the heat treatment afforded the coal in the process of pyrolysis.

A summary of typical $CO_2$ and steam gasification data obtained for graphite and several different coal chars with 10 wt. percent of binary and ternary salt catalysts added after charring is shown in Table II below:

TABLE II

Catalytic Activity of Eutectic Salts

| Salt Composition (wt. %) | m.p., °C. | Gasification Rates min$^{-1}$ × 10$^4$ | |
| --- | --- | --- | --- |
| (i) Graphite + 10 wt. % Salt: | | 700° C. | 800° C. |
| 100% $Li_2CO_3$ | 618° | 0.4 | 6.5 |
| 100% $Na_2CO_3$ | 851° | 0.08 | 1.2 |
| 100% $K_2CO_3$ | 891° | 0.1 | 2.2 |
| 100% $Na_2SO_4$ | 884° | 0.09 | 1.2 |
| 30% NaCl—70% $Na_2SO_4$ | 610° | 0.19 | 4.0 |
| 10% LiF—90% $Li_2CO_3$ | 604° | 0.28 | 6.0 |
| 40% NaCl—60% $Na_2CO_3$ | 640° | 0.18 | 5.0 |
| 50% $K_2CO_3$—50% KCl | 640° | 0.25 | 5.0 |
| (ii) Illinois #6 Char + 10 wt. % Salt: | | 600° C. | 700° C. |
| 100% $K_2CO_3$ | 891° | 0.5 | 7.0 |
| 10% LiF—90% $Li_2CO_3$ | 604° | 0.09 | 1.3 |
| 40% NaCl—60% $Na_2CO_3$ | 640° | 0.25 | 6.5 |
| 50% $K_2CO_3$—50% KCl | 640° | 0.23 | 4.0 |
| 31% NaCl—69% $Na_2SO_4$ | 610° | 0.33 | 5.0 |
| 32% $Li_2CO_3$—33% $Na_2CO_3$—35% $K_2CO_3$ | 400° | 0.4 | 7.7 |
| 37% $Na_2SO_4$—35% NaCl—28% $Na_2CO_3$ | 612° | 0.4 | 5.6 |
| (iii) Pittsburgh Char + 10 wt. % Salt: | | 700° C. | 800° C. |
| 100% $K_2CO_3$ | 891° | 0.1 | 2.0 |
| 32% $Li_2CO_3$—33% $Na_2CO_3$—35% $K_2CO_3$ | 400° | 0.45 | 8.0 |

(B) Steam Gasification
(i) Graphite + 10 wt. % Salt:

TABLE II-continued

Catalytic Activity of Eutectic Salts

| Salt Composition (wt. %) | m.p., °C. | Gasification Rates min$^{-1}$ × 10$^4$ | |
| --- | --- | --- | --- |
| | | 700° C. | 800° C. |
| 100% $K_2CO_3$ | 891° | 0.7 | 6.7 |
| 32% $Li_2CO_3$—33% $Na_2CO_3$—35% $K_2CO_3$ | 400° | 2.5 | 20.0 |
| (ii) Illinois #6 Char + 10 wt. % Salt: | | 600° C. | 700° C. |
| | | (3rd Cycle Data) | |
| 100% $K_2CO_3$ | 891° | 0.4 | 6.0 |
| 32% $Li_2CO_3$—33% $Na_2CO_3$—35% $K_2CO_3$ | 400° | 2.7 | 20.0 |
| (iii) Pittsburgh Char + 10 wt. % Salt | | 600° C. | 700° C. |
| | | (3rd Cycle Data) | |
| 100% $K_2CO_3$ | 891° | 0.1 | 1.2 |
| 32% $Li_2CO_3$—33% $Na_2CO_3$—35% $K_2CO_3$ | 400° | 2.4 | 15.0 |
| (iv) Anthracite Char + 10 wt. % Salt: | | 600° C. | 700° C. |
| | | (3rd Cycle Data) | |
| 100% $K_2CO_3$ | 891° | 1.0 | 7.5 |
| 32% $Li_2CO_3$—33% $Na_2CO_3$—35% $K_2CO_3$ | 400° | 1.4 | 13.0 |

In Table II, gasification data are listed at two representative temperatures and data for pure salt additions are included for comparison purposes. The eutectic phases were prepared by melting the appropriate salt mixtures in porcelain crucibles at 700° C. for a period of two hours. After cooling, the solidified melts were ground and physically mixed with the graphite and char to give a total concentration of 10 percent by weight of the eutectic compositions.

The invention binary and ternary eutectic catalysts exhibit catalytic activities greater than that expected for physical mixtures of the salt constituents at the same concentration, and several of the invention eutectic catalysts are significantly more catalytically active than pure $K_2CO_3$ at a 10 wt. percent concentration. The magnitude of the improvement varies, however, among the different carbonaceous substrates or carriers.

Typically, pyrolysis is conducted by loading the coal into a pyrolysis vessel, which is placed in a thermostatically controlled furnace. After establishment of an inert atmosphere, the coals are pyrolyzed at an indicated 700±2° C. In a typical case, the heating rate averaged 11.3° C./min and after two hours, the contents of the pyrolysis vessel were quenched at an average of 62.5° C./min to 200° C. and removed.

The activity of a given concentration of alkali salt eutectic catalyst in promoting the gasification of a given coal char is not strongly dependent on the mode of addition of the catalyst species to the char substrate. Thus, reactivities of char-catalyst mixtures were only slightly greater when the alkali salt eutectic catalyst was added prior to charring rather than physically mixed with the char after pyrolysis. Other techniques of catalyst addition, such as, vacuum impregnation of aqueous solutions of the salts, result in approximately the same reactivities as those resulting from mechanical mixing of the char and solid alkali salt eutectic catalyst. Apparently during gasification the catalyst particles attain a fairly uniform degree of dispersion on the char surface regardless of the method used to introduce the catalyst.

The invention binary and ternary alkali salt eutectic mixtures are more active catalysts (by factors of 2 to 5) than the pure salt components at the same concentrations. The enhancement effect, which is more pronounced in $CO_2$ than in steam gasification, appears to be related to the lower melting point of the salt phase which facilitates contact between the catalyst and the carbon substrate. A 400° C. ternary eutectic salt mixture is also an excellent catalyst in a packed bed reactor when compared to the uncatalyzed char; however, when compared to the same loading of $K_2CO_3$ held at high temperature for more than 2 hours, the eutectic is no more effective.

Other advantages of the invention process are: using a catalyst permits efficient heat integration and minimizes heat input requirements, as well as promotes a one-step gasification and methanation; Oxygen, which costs money and can cause coal-ash slagging, is not required; no pyrolysis liquids are produced; the process operates at moderate temperatures; and scaling up fluidized-bed reactors to very large sizes is relatively easy, so that comparatively few units are required for a commercial facility.

The foregoing description of preferred embodiments of the invention has been presented for purposes of illustration and description. It is not intended to be exhaustive or to limit the invention to the precise form disclosed, and obviously many modifications and variations are possible in light of the above teachings. The embodiments were chosen and described in order to best explain the principles of the invention and its practical application to thereby enable one skilled in the art to best utilize the invention in various embodiments and with various modifications as are suited to the particular use contemplated. It is intended that the scope of the invention be defined by the claims appended hereto.

What is claimed is:

1. A catalyst for use in the process of producing methane from particulate carbonaceous material, comprising a catalyst composition deposited on surface portions of said particulate carbonaceous material and formed of a mixture of alkali metal salts consisting essentially of at least one of an alkali metal carbonate and an alkali metal sulfate together with at least one of an alkali metal halide and an alkali metal carbonate differing from the first-mentioned alkali metal carbonate, said catalyst composition being prepared from a solidified melt of said mixture of alkali metal salts formed prior to being deposited upon said particulate carbonaceous material and with the alkali metal salts forming said mixture each being in a concentration adequate to render the resulting catalyst composition eutectic.

2. The catalyst claimed in claim 1, wherein the alkali metal carbonates are selected from the group consisting of $Cs_2CO_3$, $K_2CO_3$, $Na_2CO_3$, $Li_2CO_3$ and $Rb_2CO_3$, wherein the alkali metal halide is selected from the group consisting of KCl, KF, LiCl, NaCl, and NaF and wherein the alkali metal sulfate is selected from the group consisting of $Na_2SO_4$, $K_2SO_4$, $Cs_2SO_4$ and $Li_2SO_4$.

3. The catalyst claimed in claim 2, wherein the catalyst composition is a binary composition selected from the group consisting of (1) NaCl—about 60 wt.% $Na_2CO_3$, (2) NaCl—about 70 wt.% $Na_2SO_4$, (3) LiF—about 90 wt.% $Li_2CO_3$, and (4) $K_2CO_3$—about 50 wt.% KCl.

4. The catalyst claimed in claim 2, wherein the catalyst composition is a ternary composition selected from the group consisting of (1) about 32 wt.% $Li_2CO_3$—about 33 wt.% $Na_2CO_3$—about 35 wt.% $K_2CO_3$, and (2) about 37 wt.% $Na_2SO_4$—about 35 wt.% NaCl—about 28 wt.% $Na_2CO_3$.

5. The catalyst claimed in claim 1, wherein the mixture of alkali metal salts is melted to form the eutectic catalyst composition which is then solidified and ground into particulate form prior to deposition of the resulting particulates of the eutectic catalyst composition on the particulate carbonaceous material.

* * * * *